(12) United States Patent
Eggers

(10) Patent No.: US 6,569,095 B2
(45) Date of Patent: May 27, 2003

(54) ADAPTIVE SELECTION OF A WARNING LIMIT IN PATIENT MONITORING

(75) Inventor: Philip N. Eggers, Poway, CA (US)

(73) Assignee: CardioNet, Inc., San Diego, CA (US)

(*) Notice: Subject to any disclaimer, the term of this patent is extended or adjusted under 35 U.S.C. 154(b) by 0 days.

(21) Appl. No.: 09/841,153

(22) Filed: Apr. 23, 2001

(65) Prior Publication Data

US 2002/0156352 A1 Oct. 24, 2002

(51) Int. Cl.[7] ................................................ A61B 5/07
(52) U.S. Cl. ....................................... 600/300; 128/903
(58) Field of Search ................................ 600/300, 301, 600/481, 529, 508, 545; 128/903, 904

(56) References Cited

U.S. PATENT DOCUMENTS

| | | | | |
|---|---|---|---|---|
| 5,423,869 A | * | 6/1995 | Poore et al. | 607/18 |
| 5,487,755 A | * | 1/1996 | Snell et al. | 607/27 |
| 5,549,113 A | * | 8/1996 | Halleck et al. | 128/903 |
| 5,959,529 A | | 9/1999 | Kail, IV | |
| 6,088,608 A | * | 7/2000 | Schulman et al. | 600/345 |

* cited by examiner

*Primary Examiner*—Henry C. Yuen
*Assistant Examiner*—Mahmoud Gimie
(74) *Attorney, Agent, or Firm*—Thomas E. Coverstone, Esq.; Procopio, Cory, Hargreaves & Savitch, LLP.

(57) ABSTRACT

A patient is monitored by establishing a current warning limit for a physiological characteristic of the patient, providing a sensor for the physiological characteristic, and measuring a measured value of the physiological characteristic of the patient using the sensor. A revised warning limit is selected responsive to at least one of the steps of providing and measuring. The revised warning limit is then typically substituted for the current warning limit. The current warning limit serves to trigger some action in the event that the measured value of the physiological characteristic is not within an acceptable range defined by the current warning limit.

18 Claims, 2 Drawing Sheets

ADAPTIVE SELECTION OF A WARNING LIMIT IN PATIENT MONITORING

This invention relates to the monitoring of a physiological characteristic of a patient, and, more particularly, to establishing a warning limit that may be used to indicate a variation of the physiological characteristic that necessitates immediate attention.

BACKGROUND OF THE INVENTION

Advances in sensor technology, electronics, and communications have made it possible for physiological characteristics of patients to be monitored even when the patients are ambulatory and not in continuous, direct contact with a hospital monitoring system. For example, U.S. Pat. No. 5,959,529 describes a monitoring system in which the patient carries a remote monitoring unit with associated physiological sensors. The remote monitoring unit conducts a continuous monitoring of one or more physiological characteristics of the patient according to the medical problem of the patient, such as the heartbeat and its waveform.

Under prescribed conditions, the remote monitoring unit contacts a central unit to communicate information on the condition of the patient. The communication may be accomplished in some cases on a routine reporting basis (e.g., a regular once-a-day report at night on a land telephone line while the patient sleeps) and in other cases on an urgent basis that signifies an event wherein the patient may need immediate attention (e.g., over a cellular telephone link as the patient experiences discomfort or an attack). The remote monitoring unit contains logic, which may be generally be described as a warning limit, that is used to determine whether the communication is to be made on an urgent basis. The warning limit is usually based both on the nature of an evaluation criterion for specific events and also on a quantitative threshold for the selected criterion.

In the studies leading to the present invention, the inventor has observed that the application of these fundamental principles of warning limits is straightforward conceptually but complex in practice. Although many physiological characteristics may be described in a textbook manner, large variations from the textbook description are encountered in everyday situations. For example, variations in sensor performance, individual human characteristics and responses, personal experiences, and the like make it difficult to establish warning limits that are universally applicable, or even applicable for the same patient under all conditions.

The warning limits are normally selected in a conservative manner when viewed from the standpoint of patient safety. That is, it is preferable to make urgent communications more often than necessary, rather than to fail to make an urgent communication when it is necessary. On the other hand, too many urgent communications are wasteful in terms of power consumption of the remote monitoring unit (establishing and maintaining a cell phone connection consumes a relatively large amount of power and thus reduces available battery life), telephone connection time expense, and resource use at the central unit.

For these reasons, it is important to establish realistic warning limits characteristic of situations that are truly urgent. There are not currently available any approaches which meet this requirement, and consequently a need exists for establishing warning limits for use in such situations. The present invention fulfills this need, and further provides related advantages.

SUMMARY OF THE INVENTION

The present approach provides a technique for monitoring a patient in which one or more warning limits are recursively reevaluated as necessary. Proposed changes to the warning limits are made without human intervention, but in some cases the proposed changes may be reviewed by a human being to be certain that they are realistic. The present approach is fully compatible with adjustments to warning limits made by medical personnel. The present approach allows a patient monitoring system to be continuously refined and customized for the individual patient and the individual monitoring system through an adaptive learning process.

In accordance with the invention, a method of monitoring a patient comprises the steps of establishing a current warning limit for a physiological characteristic of the patient. A sensor is provided for the physiological characteristic. such as the heartbeat, for example, and a measured value of the physiological characteristic of the patient is measured using the sensor. The measured value and the current warning limit are compared, and a warning signal may be generated responsive to the step of comparing in the event that the measured value is outside the value defined by the current warning limit. The method includes selecting a revised warning limit responsive to at least one of the steps of providing and measuring, preferably without human intervention (i.e., automatically). However, a human being may review the revised warning limit. That is, the automated system may propose the revision, subject to revision by the human being.

The step of selecting a revised warning limit may be made responsive to any of a wide variety of circumstances. For example, the operating characteristics of the sensor may be determined, and the selecting of the revised warning limit may be made responsive to the determination of the operating characteristics of the sensor. The selecting of a revised warning limit may instead be responsive to the step of measuring, as where the step of measuring is performed as a function of time, and wherein the step of selecting is responsive to time variations in the measured value or is responsive to a value of time. The selecting of the revised warning limit may be additionally responsive to a second physiological characteristic or to a patient history.

In one embodiment, the present invention is practiced using a monitoring apparatus including a remote monitoring unit associated with the patient, a central unit, and a communications device which selectively establishes a communications link between the remote monitoring unit and the central unit responsive to a warning signal. This apparatus provides a real-time urgent communications capability. It may also be practiced in other operable situations, such as monitors whose data are periodically transmitted, non-ambulatory situations, and the like.

The present invention allows the patient to be monitored and acceptable limits for the physiological conditions of the patient to be defined increasingly precisely over time. With continued experience as the monitoring apparatus adapts to the individual patient, the incidence of unnecessary urgent communications is expected to decrease. The result is that the efficiency of resource utilization is expected to increase over time. Additionally, the monitoring apparatus discovers which warning limits are most meaningful for the individual patient, so that the precision of the generation of warnings is increased.

Other features and advantages of the present invention will be apparent from the following more detailed descrip-

DETAILED DESCRIPTION OF THE INVENTION

Figure 1:
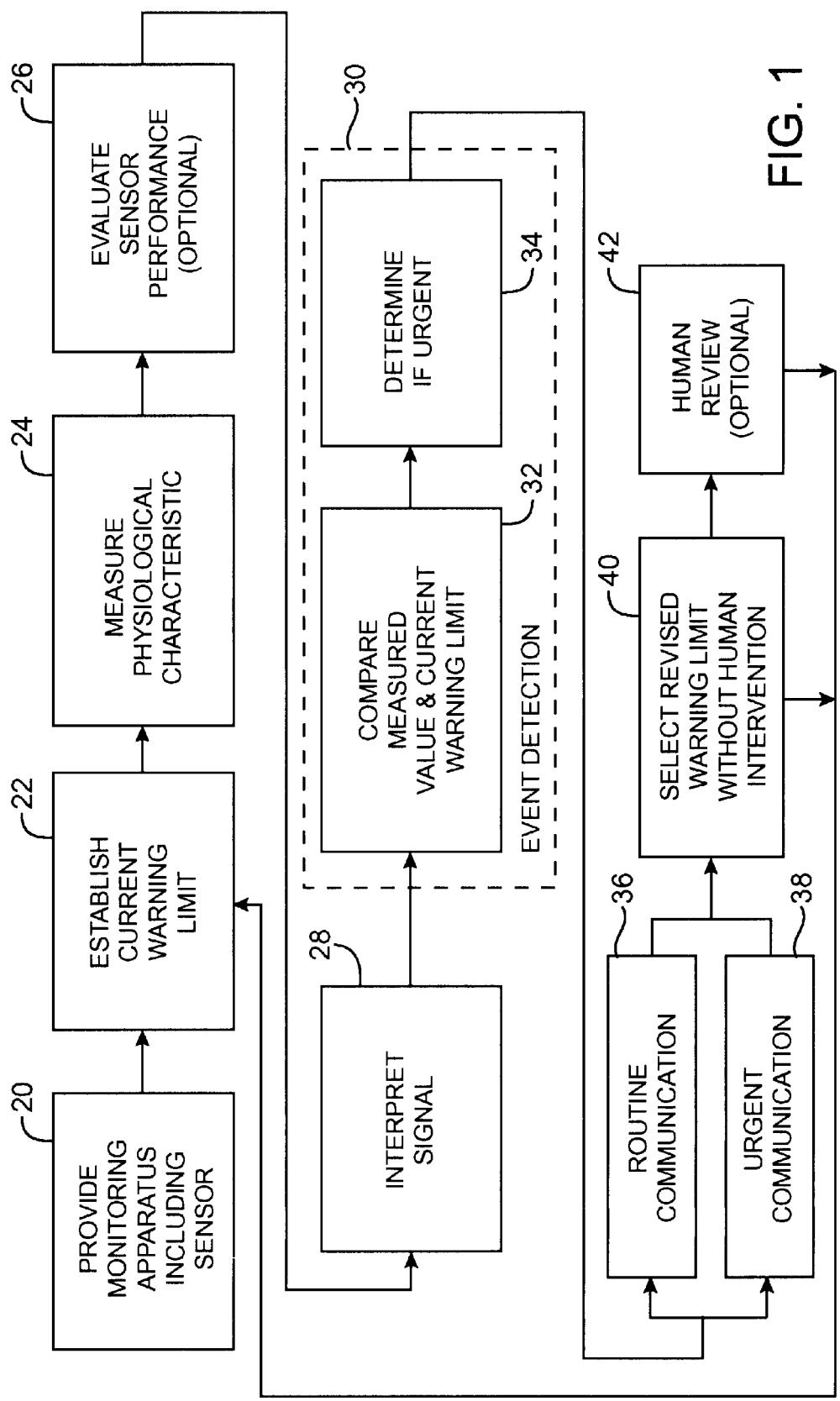
FIG. 1 is a block flow diagram of a method for practicing the present approach.
Figure 2:
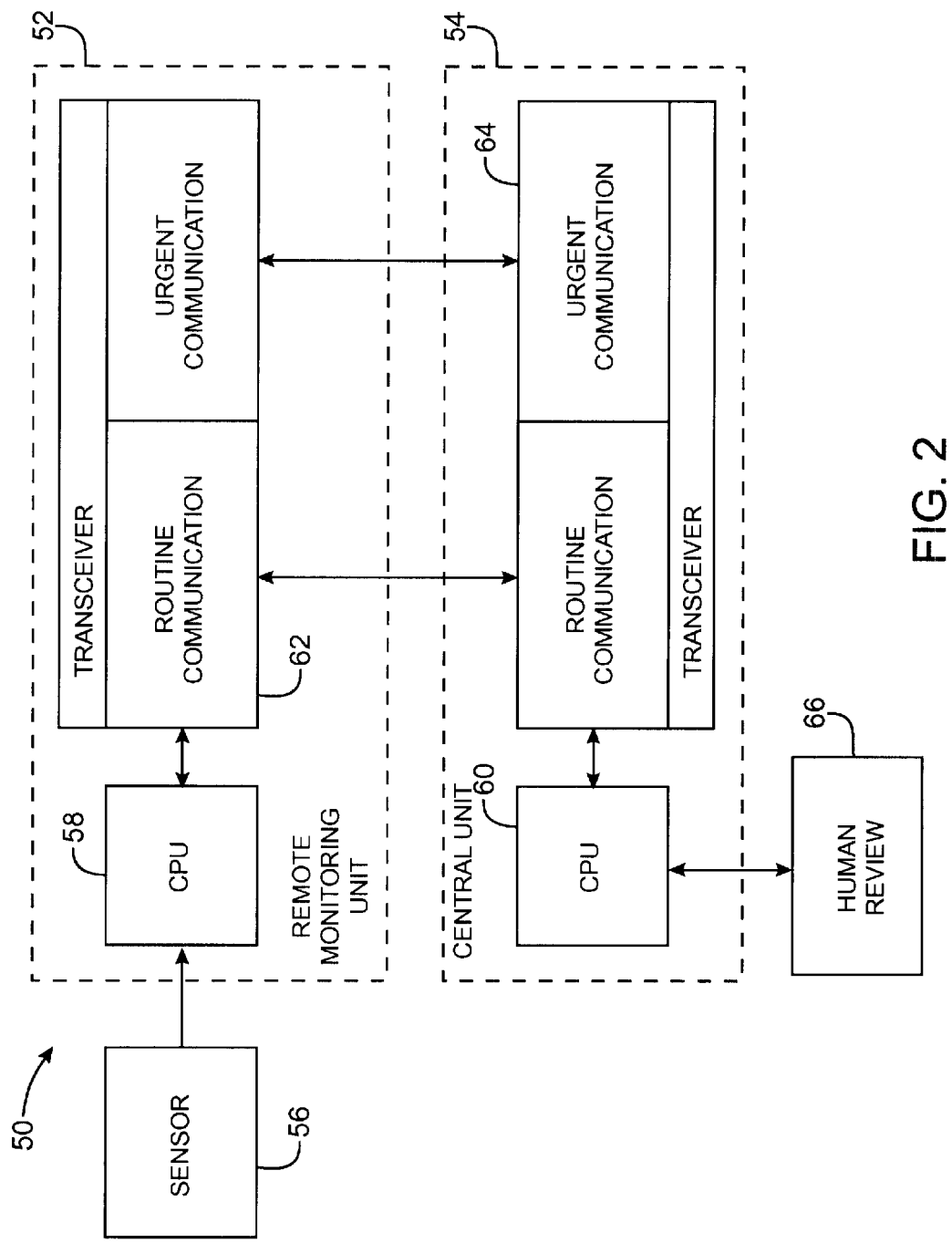
FIG. 2 is a simplified schematic block diagram of a preferred apparatus with which the present invention may be used.

FIG. 1 depicts an approach for practicing the present invention. A monitoring apparatus is provided, numeral 20. The monitoring apparatus may be of any operable form, and one preferred form of the monitoring apparatus 50 is illustrated in FIG. 2. The monitoring apparatus 50 is shown in a simplified form illustrating only those portions that are required to discuss the present invention. The monitoring apparatus 50 is generally like that disclosed in U.S. Pat. No. 5,959,529, whose disclosure is incorporated by reference, but modified as discussed herein.

The monitoring apparatus 50 includes a remote monitoring unit (RMU) 52 carried by an ambulatory patient, and a central unit (CU) 54. The central unit 54 is typically a file server or a network. Other remote monitoring units, that are not "portable" but may be at a fixed location in a patient's home or hospital facility, may be used as well. A sensor 56 measures a physiological characteristic of a patient, and is typically in contact with the patient. ("Patient" is used in a broad sense, and refers to a person being monitored.) There may be one sensor or more than one sensor 56, depending upon the parameters of the patient that are of interest. Examples of operable sensors 56 include a heart monitor sensor, a blood pressure monitor sensor, a temperature monitor sensor, a respiration sensor, a brain wave sensor, a blood chemistry sensor, a blood glucose sensor, a blood oxygen saturation sensor, a patient position sensor, and a patient activity sensor. Sensors of various types are known in the art, and details of their construction and operation does not form a part of the present invention.

In either event, the sensor 56 is in communication with a central processing unit (CPU) 58 of the remote monitoring unit 52, with intermediate signal conditioning equipment as necessary (not shown here). The central processing unit 58 performs analyses of the signals of the sensor 56, as will be discussed subsequently. Similarly, the central unit 54 includes a central processing unit (CPU) 60 to perform calculations and analyses, as will be discussed subsequently. (As noted, the central unit 54 and its CPU 60 may be of any operable type, such as a dedicated system, a network, or a file server.) The remote monitoring unit 52 and the central unit 54 may be placed in two-way communication with each other through a transceiver 62 located in the remote monitoring unit 52 and a communicating transceiver 64 located in the central unit 54. The transceivers 62, 64 may include any operable type of communications devices. For example, they may include a modem to establish communications over a conventional land-line telephone for routine communications. They may also include a cellular telephone transceiver to establish communications on an urgent basis. The transceivers 62, 64 may also be equipped for two-way voice communication between the patient and a person at the central unit 54. The present invention is concerned in part with establishing the criteria for determining when a communication should be routine or urgent, by adaptively selecting the warning limits that signal a need for an urgent communication. The central unit 54 is provided with an interface to allow human review 66 of recommended actions of the central processing unit 60, as by the patient's physician.

Returning to the discussion of FIG. 1, a current warning limit is established, numeral 22. The current warning limit relates to the type of physiological condition being monitored by the sensor 56. In the case of a heart sensor that measures a voltage as a function of time, for example, the warning limit may relate to any of a wide variety of types of information that may be determined from the heart sensor output to the central processing unit 58. Examples of warning limits may include, for example, the frequency of heartbeats, the shape of a particular part of the heartbeat waveform, the amplitude of a particular part of the heartbeat signal, or any other feature of the signal. There may also be quantitative values placed on some of these types of warning limits, such as a maximum or minimum number of heartbeats per minute, a maximum or minimum amplitude, a maximum number of features of a particular shape or type per minute (or hour), etc. The current warning limit is normally established in step 22 as input values from the experience of the medical caregiver responsible for the patient.

The physiological characteristics of the patient are measured using the sensor 56, numeral 24, and provided to the central processing unit 58. In the case of a heartbeat sensor, for example, the data output is a series of data pairs of sensor voltage output as a function of time (provided by a clock in the central processing unit 58).

The central processing unit 58 preliminary evaluates the sensor signals. It optionally evaluates the sensor performance, numeral 26. For example, it is known that the performance of some sensors degrades over time. That is, if a single feature such as the same heartbeat is measured by two sensors that are otherwise identical but wherein one has been used for five days and the other is new, the output voltages of the two sensors typically vary. If a warning limit is based on this voltage output, then different performance will be obtained for the used sensor and the new sensor. The change of performance of the sensor may be tracked by any operable approach, such as calibration signals or historical information. The sensor evaluation of step 26 keeps track of these changes over time.

The sensor signal is interpreted, numeral 28. The interpretation step 28 extracts the type of information of interest from the sensor signal. For example, if the information of interest is the frequency of heartbeats, a counting procedure is used. If the information of interest is a shape of the voltage-time output, then curve-shape analysis procedures are used. The methodology of such interpretation techniques is known in the art.

Using this information, event detection is performed, numeral 30. Event detection preferably includes comparing the measured value of a feature from the interpretation step 28 with the current warning limit for that feature as provided in step 22. For example, it may be significant if the heartbeat rate exceeds 100 per minute, or if more than a selected number of heartbeat shapes occurs per minute or per hour. Comparisons of other measured physiological characteristics, such as respiration rate, blood pressure, and the like may be made as well.

The comparisons with the current warning limits are used to determine whether an event is occurring that requires urgent communication between the remote monitoring unit 52 and the central unit 54, numeral 34. The determination may be based on a single variable or multiple variables. For example, if the heartbeat exceeds a heartbeat warning limit value and the blood oxygen saturation level also exceeds a blood oxygen warning limit value, then an urgent communication may be called for. Based on this determination, the data is stored for a later routine communication, numeral 36, or the transceivers 62, 64 are activated for an urgent transmission to the central unit 54, numeral 38.

The current warning limit determines whether the remote monitoring unit 52 will establish a telephonic or other communication link with the central unit 54 on an urgent, immediate basis. In that event, the central unit 54 will be called upon to provide assistance to the patient, either directly or by contacting an emergency service provider, or it may determine that in fact no emergency exists. It is important that an urgent communication be established when an emergency truly exists. It is also desirable that instances of establishing communications where no emergency exists be minimized in order to conserve battery power of the remote monitoring unit, to minimize unnecessary cellular telephone time charges, and to minimize the use of medical personnel who may be called upon unnecessarily to review situations that are not truly emergencies.

To improve the efficiency of the system, revised warning limits are selected, preferably but not necessarily without human intervention (i.e., "automatically"), numeral 40. This selection may be performed by the remote monitoring unit 52 in some cases and by the central unit 54 via the communication link in other cases. Some revisions to the warning limits are mechanical in nature and almost certainly do not require any human review. For example, if the sensitivity of the sensor changes over time so that a voltage output threshold warning limit that formerly was 9.60 millivolts is to be altered to 9.55 millivolts in order to keep the system sensitive to a constant level of signal amplitude, the change in the warning limit may typically be made by the remote monitoring unit 52. On the other hand, a change that is more closely associated with a medical condition is more likely to require a medical review. Thus, if a heartbeat frequency warning limit of 100 beats per minute is to be changed to 120 beats per minute based on extended experience in order to obtain a better indicator of when urgent communication is required, it is preferred that the central processing unit 60 of the central unit 54 make a recommendation based upon data analysis and without human intervention, and then a human being in the form of the patient's doctor or a medical technician approve the change under the human review 66. Typically, such changes based upon a medical evaluation occur relatively infrequently and may be made responsive to a routine communication rather than an urgent communication.

A wide variety of grounds for a selection of a revised warning limit are possible, but they generally fall into several classes.

One ground is related to instrumentation, with an example being the change in sensor sensitivity discussed above.

Another ground is a change in a warning limit based on a single-valued measured physiological characteristic. For example, a warning limit of 100 beats per minute may be a significant predictor of distress and an emergency for a first patient, but a second patient may naturally have a higher heart rate slightly above this warning limit so that a warning limit of 100 beats per minute produces many unnecessary urgent communications. Experience gained over time with the second patient will establish a more realistic warning limit for the second patient.

Another ground is a correlation between two or more measured physiological characteristics. For example, a heartbeat rate in excess of 100 beats per minute may signify distress if the patient is at rest and the respiration rate is less than 15 breaths per minute. A heartbeat in excess of 100 beats per minute may be quite normal if the patient is exercising and the respiration rate is equal to or greater than 15 breaths per minute. On the other hand, in the latter case a heartbeat in excess of 130 beats per minute even with a respiration rate faster than 15 breaths per minute may signal an emergency. The heartbeat warning limit may thus be selected responsive to the respiration rate.

Another ground is a correlation of a measured physiological characteristic with a nonphysiological parameter. For example, a heartbeat of 100 beats per minute may be quite normal for 16 hours per day, but during sleep periods from 11 pm to 7 am such an increase in the sleeping heartbeat rate to 100 beats per minute may signify an emergency. The warning limit may therefore correlate to absolute time according to daytime/nighttime activity, or it may correlate to a Circadian rhythm of the patient. In another example, if the remote monitoring unit is equipped with an accelerometer, a heartbeat rate in excess of 100 beats per minute coupled with a high temporary accelerometer reading may indicate that the patient has fallen and is injured but unable to otherwise communicate.

Another ground is a complete change in the information required from the interpretation step 28. It may initially be believed that a good objective correlator of distress in a patient is a heartbeat rate. Over time, however, it is found that the occurrence of more than three premature ventricular contractions (PVCs) per hour is a more dependable predictor of distress in the patient and an emergency situation. The interpretation step 28 is therefore shifted from a heartbeat count to a waveshape analysis.

The present invention is not intended to identify each specific type of revision that may be made in the warning limits. In fact, there are as many possibilities for types of revisions as there are patients to be monitored. The point of the present invention is to provide a technique and a methodology to allow an adaptive updating of the decision making of the monitoring apparatus as to whether an urgent communication is required instead of a routine communication.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A method of monitoring a patient, comprising the steps
   establishing a current warning limit for a physiological characteristic of the patient;
   providing a sensor for the physiological characteristic;
   measuring a measured value of the physiological characteristic of the patient using the sensor;
   comparing the measured value and the current warning limit, and generating a warning signal responsive to the step of comparing; and
   selecting a revised warning limit responsive to at least one of the steps of providing and measuring.

2. The method of claim 1, including an additional step, after the step of selecting, of a human being reviewing the revised warning limit.

3. The method of claim 1, wherein the step of providing includes the steps of obtaining the sensor, and determining the operating characteristics of the sensor, and wherein the step of selecting is responsive to the step of determining the operating characteristics of the sensor.

4. The method of claim 1, wherein the step of selecting is responsive to the step of measuring.

5. The method of claim 1, wherein the step of measuring is performed as a function of time, and wherein the step of selecting is responsive to a value of time.

6. The method of claim 1, wherein the step of selecting is additionally responsive to a second physiological characteristic.

7. The method of claim 1, wherein the step of selecting is additionally responsive to a patient history.

8. The method of claim 1, including an additional step of providing a monitoring apparatus including a remote monitoring unit associated with the patient, a central unit, and a communications device which selectively establishes a communications link between the remote monitoring unit and the central unit responsive to a warning signal, and wherein the step of selecting is performed at least in part by the central unit.

9. The method of claim 1, wherein the physiological characteristic is a characteristic of the heart.

10. The method of claim 1, wherein the step of selecting is performed without human intervention.

11. A method of monitoring a patient, comprising the steps of providing a monitoring apparatus including a remote monitoring unit associated with the patient, a central unit, and a communications device which selectively establishes a communications link between the remote monitoring unit and the central unit responsive to a warning signal;

establishing a current warning limit for a physiological characteristic of the patient;

providing a sensor for the physiological characteristic as a part of the remote monitoring unit;

measuring a measured value of the physiological characteristic of the patient using the sensor;

comparing the measured value and the current warning limit;

generating a warning signal responsive to the step of comparing;

selecting a revised warning limit responsive to at least one of the steps of providing a sensor, comparing, and measuring, and substituting the revised warning limit for the current warning limit, the step of selecting being performed at least in part by the central unit; and repeating the steps of providing a sensor, measuring, and comparing.

12. The method of claim 11, including an additional step, after the step of selecting, of a human being reviewing the revised warning limit.

13. The method of claim 11, wherein the step of providing includes the steps of obtaining the sensor, and determining the operating characteristics of the sensor, and wherein the step of selecting is responsive to the step of determining the operating characteristics of the sensor.

14. The method of claim 11, wherein the step of selecting is responsive to the step of measuring.

15. The method of claim 11, including an additional step, after the steps of providing and measuring, of comparing the measured value and the current warning limit, and generating a warning signal responsive to the step of comparing.

16. The method of claim 11, wherein the step of selecting is performed without human intervention.

17. A method of monitoring a patient, comprising the steps of establishing a current warning limit for a physiological characteristic of the patient;

providing a sensor for the physiological characteristic;

evaluating the characteristics of the sensor as a function of time;

measuring a measured value of the physiological characteristic of the patient as a function of time using the sensor;

comparing the measured value and the current warning limit generating a warning signal responsive to the step of comparing; and selecting a revised value of the warning limit responsive to at least one of the steps of providing and measuring.

18. The method of claim 17, wherein the step of selecting is performed without human intervention.

* * * * *